United States Patent [19]
Kendall

[11] Patent Number: 5,458,625
[45] Date of Patent: Oct. 17, 1995

[54] TRANSCUTANEOUS NERVE STIMULATION DEVICE AND METHOD FOR USING SAME

[76] Inventor: Donald E. Kendall, 6105 Lake Lindero Dr., Agoura, Calif. 91301

[21] Appl. No.: 238,840

[22] Filed: May 4, 1994

[51] Int. Cl.$^6$ .................................................. A61N 1/36
[52] U.S. Cl. ............................... 607/46; 607/63; 607/58
[58] Field of Search ............................... 607/45, 46, 58, 607/74, 63

[56] References Cited

U.S. PATENT DOCUMENTS

| | | | |
|---|---|---|---|
| 4,595,010 | 6/1986 | Radke | 607/74 |
| 4,719,922 | 1/1988 | Padjen et al | 607/45 |

*Primary Examiner*—William E. Kamm
*Assistant Examiner*—Scott M. Getzow
*Attorney, Agent, or Firm*—John J. Posta, Jr.

[57] ABSTRACT

A device for use in providing transcutaneous nerve stimulation and a related method of use are disclosed which may be utilized to stimulate superficial sprigs of the Vagal nerve located in the auricle of the ear for the alleviation of substance withdrawal symptoms or the provision of pain relief, stress relief, and/or general muscle relaxation. The device uses two pairs of transcutaneous pad electrodes, with one pair of the transcutaneous pad electrodes being located on each of the two clips which are applied to the lobes of each ear, with the device then supplying an adjustable amplitude, adjustable repetition rate bipolar pulse train for a predetermined length of time to the transcutaneous pad electrodes on the clips. The device includes safety features whereby the treatment must be initiated with the initial amplitude of the output pulses set to zero and adjusted upward, and wherein the length of the treatment cycle is limited in duration and cannot be restarted without first resetting the device by turning it off and then on again.

20 Claims, 2 Drawing Sheets

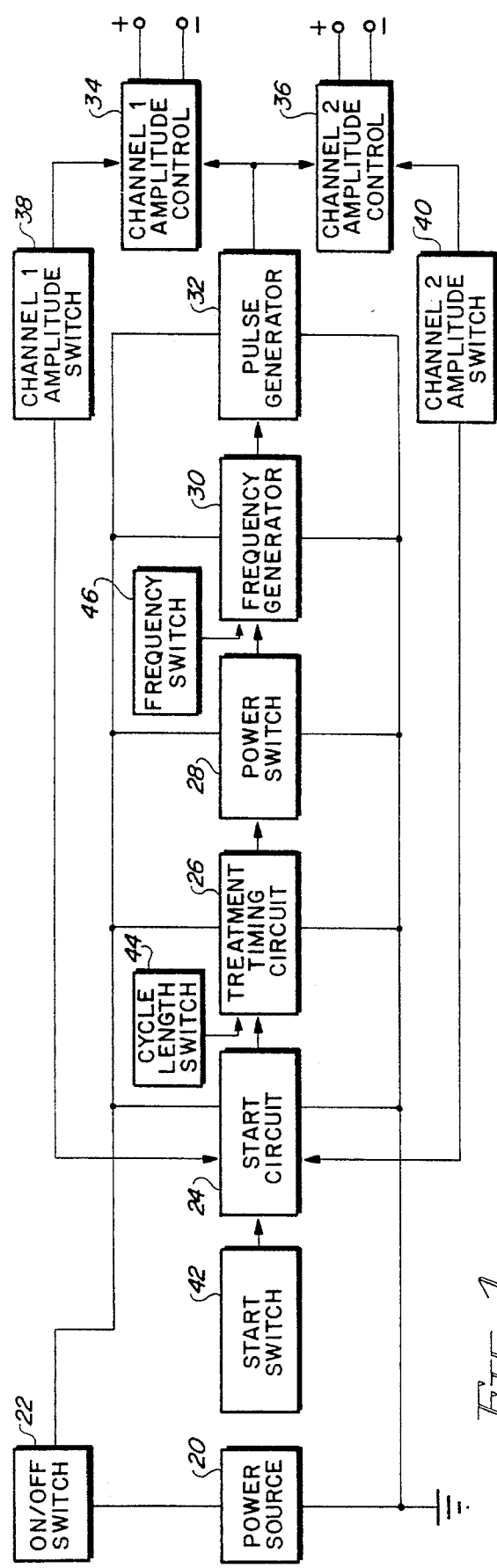
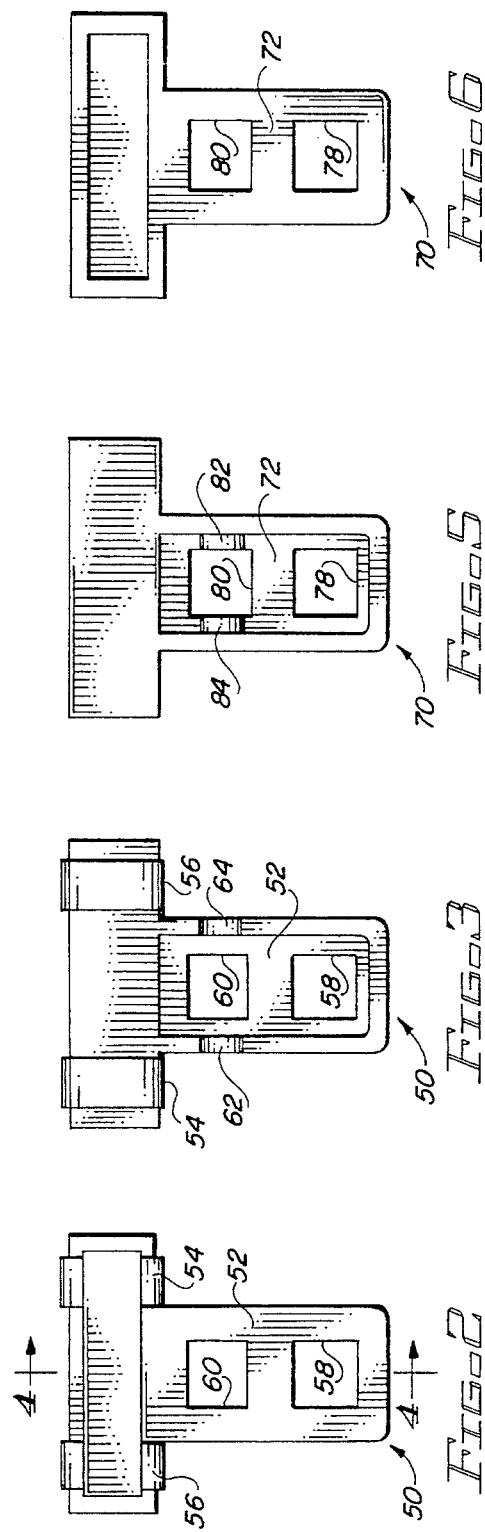

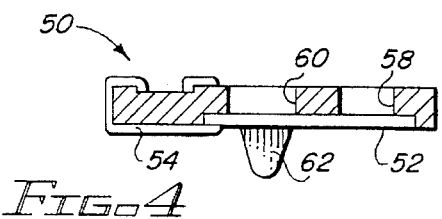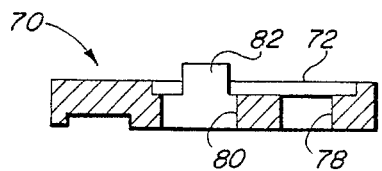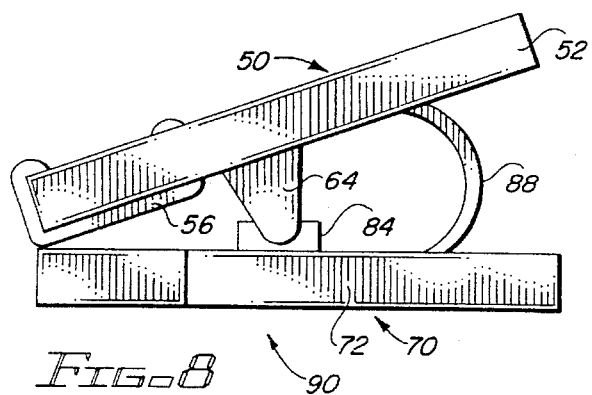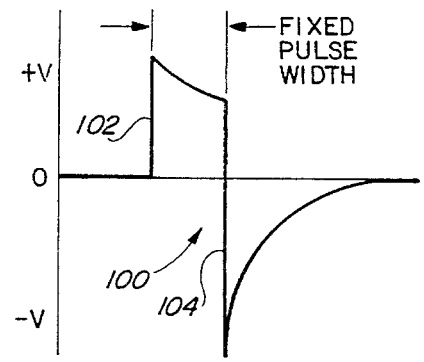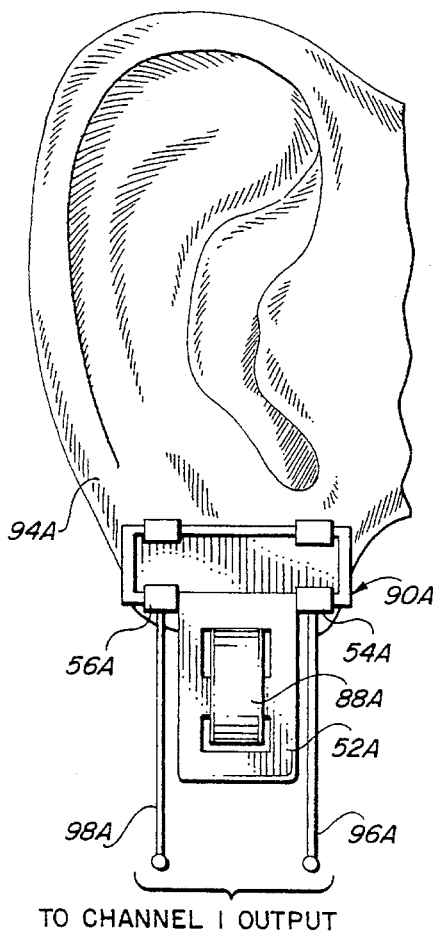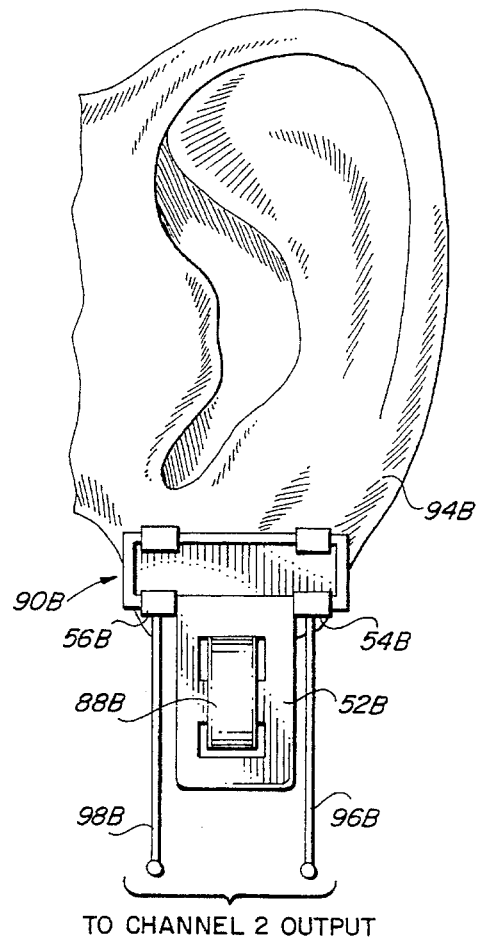

TRANSCUTANEOUS NERVE STIMULATION DEVICE AND METHOD FOR USING SAME

BACKGROUND OF THE INVENTION

FIELD OF THE INVENTION

The present invention relates generally to transcutaneous electrical nerve stimulation (TENS), and more particularly to a device for providing stimulation of superficial sprigs of the Vagal nerve located in the auricle of the ear, and also to a related method of providing such nerve stimulation.

Various afflictions of the central nervous system have caused a great deal of distress to people for all of recorded history. Such conditions include, but are not limited to, emotionally or environmentally induced stress, the presence of long-term pain due to a variety of conditions, muscle tension resulting in general unease, and withdrawal symptoms resulting from addiction to a variety of substances, including nicotine, alcohol, cocaine, opiates, etc. In addition to the more traditional medical therapies such as pharmacological therapy and psychological therapy which have been used to treat these various conditions in people around the world, there exist several less conventional techniques of treating these conditions. Examples of the more unconventional therapies include acupuncture and functional electrical stimulation (FES).

Acupuncture is only recently gaining acceptance in the West, although it has been utilized in China for over 2500 years. Only recently have advances in neuroscience provided a physiological basis for explaining the mechanisms used in acupuncture. Channel phenomena, viscerosomatic relationships, and other mechanisms which bring about beneficial effects are facilitated by the use of acupuncture. The use of acupuncture has long been known to provide medium term relief of pain, and even analgesia for the facilitation of surgery.

For a review of the historical relevance of acupuncture, a two-part article entitled, "A Scientific Model for Acupuncture" may be found in the *American Journal of Acupuncture*, Vol. 17, No. 3, at pages 251–268 (July–September 1989), and in the American Journal of Acupuncture, Vol. 17, No. 4, at pages 343–360 (1989). This article is hereby incorporated herein by reference.

More recently, various papers have been published which observe that acupuncture may be utilized to provide relief from the symptoms of substance addiction. These findings, which have only been made in the last two decades, have demonstrated that the use of acupuncture may alleviate the symptoms of abstinence syndrome brought on by acute withdrawal from drugs. A high initial success rate has been achieved in detoxification for drugs including nicotine, alcohol, cocaine, marijuana, heroin, methadone, and other opiates. This work is summarized in a paper entitled, "Treatment of Substance Addiction With Acupuncture," which was presented at the Second International Congress on Chinese Medicine in Los Angeles, Calif., in July 1989, which will be published in 1994. This paper is also hereby incorporated herein by reference.

Unfortunately, there are a large number of people who have a fear of needles. While most of these people will tolerate the temporary insertion of a needle in order to inject a drug, they are unwilling to even try acupuncture, except as a last resort. The number of people willing to try acupuncture therapy diminishes even further when they are informed that treatment for addiction involves the insertion of needles into the auricle of the ear, wherein are found superficial sprigs of the Vagus nerve.

Another unconventional therapy, functional electrical stimulation, has been studied for at least several decades, although it is still in its infancy. Electrical excitation of neural tissue has been utilized both to restore missing or impaired body function, and in the treatment of pain. Examples of the former purpose include the operation of artificial prosthetic limbs to replace missing or paralyzed limbs, cochlear stimulation devices to enable an auditory sensation in the deaf, and the provision of visual sensation to the blind.

Unfortunately, the benefits of functional electrical stimulation have been relatively limited in practical application, with the devices being extremely expensive and available only in limited quantities to a small number of individuals. There have also been problems in the development of the technology caused by the polarization of body tissue due to an imbalance in the flow of electrical current through the body tissue.

One of the limited successes in the technology has been in transcutaneous electrical nerve stimulation devices, which administer electrical stimulation through electrodes applied to the skin of the individual being treated. These devices to date have not had efficient output waveforms, or optimized operating procedures. As a result, typical transcutaneous electrical nerve stimulation devices must be applied for several hours at a time, which is counterproductive to the provision of long-term pain relief. This is due to the fact that long-term stimulation can deplete certain central nervous system neurochemicals, with tolerance thereby being established. After this occurs, the transcutaneous electrical nerve stimulation devices are no longer effective.

It is accordingly the primary objective of the present invention that it provide both a device and a related method of operating the device which are capable of efficiently and effectively treating emotionally or environmentally induced stress, promoting endogenous pain control, and assisting in muscle relaxation. It is a further objective of the present invention that it provide both an apparatus and an optimized technique of applying therapy which are useful in the treatment of substance abuse, enabling the withdrawal from use of the substance with substantially minimized withdrawal symptoms. It is yet another objective of device and method of the present invention that they require only a relatively short time for treatment, both in the time required per treatment session, and in the number of treatment sessions required.

Broadly, it is an important objective of the device and the method of the present invention that they be both safe and efficacious in every way. On a more technical matter, it is an objective of the apparatus and method of the present invention that they use a principle of operation which prevents the undesirable polarization of body tissue during operation. It is a further objective of the device and method of the present invention that they not deplete neurochemicals during their operation, and that their operation not result in a tolerance for the treatment being established.

The apparatus of the present invention must be of construction which is both durable and long lasting, and it should also require little or no maintenance to be provided by the operator. In order to enhance the market appeal of the apparatus of the present invention, it should feature both inexpensive construction and inexpensive operation, to thereby afford it the broadest possible market. Finally, it is also an objective that all of the aforesaid advantages and objectives of the present invention be achieved without incurring any substantial relative disadvantage.

SUMMARY OF THE INVENTION

The disadvantages and limitations of the background art discussed above are overcome by the present invention. With this invention, the advantages of acupuncture and functional electrical stimulation have been combined at least in part, with transcutaneous electrodes being substituted for acupuncture pins, and with an electrical stimulus being provided to the transcutaneous electrodes to induce the desired effect.

In the initial design and development of the present invention, spaced-apart acupuncture needles were used to contact superficial sprigs of the Vagus nerve at two sites on the auricle of the ear. It was discovered that by stimulating the acupuncture needles placed in the ear, it was possible to successfully treat addiction, with the electrical stimulation protocol alleviating the symptoms of withdrawal from the addictive substances. Since many people have a fear of needles (particularly when they are to be inserted into the ear), another approach to stimulate the Vagus nerve was deemed to be necessary.

The alternate approach which was discovered involves the use of transcutaneous pads as electrodes instead of using needles, with the results being nearly as good without necessitating the invasive placement of needles. While the transcutaneous pads work quite well, achieving uniform placement requires proper spacing of the transcutaneous pads. Accordingly, a special spring-loaded clip is utilized, with the transcutaneous pads being located on one side of the clip. By placing the clip in the proper position on the ear, the transcutaneous pads carried by the clip are placed into proper position for stimulation of the Vagus nerve.

The two transcutaneous pads on the clip are thus utilized as electrodes to apply the electrical stimulation to the ear. The two transcutaneous pads are used with one as the signal source, and the other as the signal return, with the current passing through a short electrical pathway on the ear lobe. Electrical stimulation of this region of the ear lobe will activate small sprigs of the Vagus nerve, which travel close to the surface of the ear in the cavum concha of the auricle.

Since the relative positions of the transcutaneous pads are maintained at a small and constant distance apart by the clip, the electrical current path is restricted to a small region of the ear lobe. In the preferred embodiment, a clip with two transcutaneous pads used as electrodes is placed on each ear, with transcranial currents being effectively prevented by the short current path between pairs of the transcutaneous pads.

A stimulator is used to provide the electrical stimulation currents to each pair of the transcutaneous pads. The stimulator has two independent output circuits to further reduce the possibility of transcranial currents. The stimulator provides a signal protocol consisting of a sequence of periodic biphasic stimulation pulses. The positive areas and the negative areas of each of the stimulation pulses are equal in size, thereby ensuring that the tissue stimulated will not remain polarized. The stimulation pulses are of short duration, and also of variable amplitude.

Stimulation pulses are automatically and periodically applied over a length of time which is adjustable, but which has a maximum duration of approximately 20–45 minutes. In order to prevent the stimulation cycle from being reapplied, the stimulation unit must be turned off to reset it before it will again provide the stimulation regime. In another safety feature, the amplitude of each of the two channels must also be turned fully off before the stimulation unit will provide the stimulation regime.

A typical treatment protocol involves applying the therapy once or twice a day for two to six days when used for treatment of addiction during the withdrawal stage. This is believed to be accomplished by a restoration of disturbed vegetative response through stimulation of the Vagal centers, and by reactivating ceratin habituated nuclei within the brain stem.

If the device of the present invention is used for pain control, it promotes endogenous pain control processes by activating descending nerve fibers of the dorsal lateral funiculus of the spinal cord by certain raphe nuclei of the brain stem to presynaptically inhibit the perception of pain. The device of the present invention will also promote muscle relaxation by descending spinal inhibition of afferent proprioceptive fibers. Finally, it normalizes visceral and viscerosomatic reflexes resulting from disturbed vegetative response caused by emotionally or environmentally induced stress by directly stimulating the Vagal centers of the brain stem responsible for mediating such responses.

It may therefore be seen that the present invention teaches both a device and a related method of operating the device which are capable of efficiently and effectively treating emotionally or environmentally induced stress, promoting endogenous pain control, and assisting in muscle relaxation. Further, the apparatus and the optimized technique of applying therapy of the present invention are highly useful in the treatment of substance abuse, enabling the withdrawal from use of the substance with substantially minimized withdrawal symptoms. The device and method of the present invention also require only a relatively short treatment session, with only a relatively small number of treatment sessions being required for successful treatment.

The device and the method of the present invention are both safe and efficacious in every way. In addition, the apparatus and method of the present invention use a principle of operation which prevents the undesirable polarization of body tissue during operation. It is a further advantage of the device and method of the present invention that they do not deplete neurochemicals during their operation, and that their operation will not result in a tolerance for the treatment being established.

The apparatus of the present invention is of a construction which is both durable and long lasting, and it also requires little or no maintenance to be provided by the operator. It features both inexpensive construction and inexpensive operation, thereby enhancing its market appeal to afford it the broadest possible market. Finally, all of the aforesaid advantages and objectives of the present invention are achieved without incurring any substantial relative disadvantage.

DESCRIPTION OF THE DRAWINGS

These and other advantages of the present invention are best understood with reference to the drawings, in which:

FIG. 1 is a functional schematic block diagram of a stimulation device constructed according to the teachings of the present invention;

FIG. 2 is a top plan view of a top clip half;

FIG. 3 is a bottom plan view of the top clip half illustrated in FIG. 2, showing the two small, electroconductive, transcutaneous pads which will act as electrodes;

FIG. 4 is a sectional side view of the top clip half illustrated in FIGS. 2 and 3;

FIG. 5 is a top plan view of a bottom clip half, showing the side of the bottom clip half which will face toward the bottom of the top clip half illustrated in FIGS. 2 through 4;

FIG. 6 is a bottom plan view of the bottom clip half illustrated in FIG. 5;

FIG. 7 is a sectional side view of the top clip half illustrated in FIGS. 5 and 6;

FIG. 8 is a side view of a clip assembled from the top clip half illustrated in FIGS. 2 through 4, the bottom clip half illustrated in FIGS. 5 through 7, and a spring;

FIG. 9 is a somewhat schematic plan view illustrating how two of the clips illustrated in FIG. 8 are applied to the ear lobes of two ears; and FIG. 10 is a plot of voltage versus time showing a biphasic pulse which is supplied by each of the two independent output circuits of the stimulation device illustrated in FIG. 1 to the clips illustrated in FIG. 9.

DETAILED DESCRIPTION OF THE PREFERRED EMBODIMENT

The preferred embodiment of the stimulation device of the present invention is illustrated in FIG. 1, with one of the clips used to apply the stimulation pulses supplied by the stimulation device of FIG. 1 being illustrated in FIGS. 2 through 8. Referring first to the stimulation device and to FIG. 1, a power source 20 is used to supply power to the stimulation device illustrated. The power source 20 may comprise either a battery, or an opto-isolated supply using conventional AC line current to power the stimulation device.

One side of the power supplied by the power source 20 is supplied to a first side of an on/off switch 22. The other side of the on/off switch 22 is connected to power a start circuit 24, a treatment timing circuit 26, a power switch 28, a frequency generator 30, and a pulse generator 32. The other side of the power supplied by the power source 20 is also connected to the start circuit 24, the treatment timing circuit 26, the power switch 28, the frequency generator 30, and the pulse generator 32.

The start circuit 24 supplies a start signal to the treatment timing circuit 26, which in turn supplies a timed drive signal to the power switch 28. The power switch 28 supplies an operation signal to the frequency generator 30, which in turn supplies a pulsed signal to the pulse generator 32. The frequency generator 30 supplies a fixed amplitude pulse train to a channel 1 amplitude control 34 and to a channel 2 amplitude control 36.

The channel 1 amplitude control 34 provides a pulse train corresponding to the fixed amplitude pulse train from the pulse generator 32, but with the amplitude of the pulse train from the channel 1 amplitude control 34 being adjustable based on an input from a channel 1 amplitude switch 38. The channel 2 amplitude control 36 provides a pulse train corresponding to the fixed amplitude pulse train from the pulse generator 32, but with the amplitude of the pulse train from the channel 2 amplitude control 36 being adjustable based on an input from a channel 2 amplitude switch 40. The channel 1 amplitude switch 38 and the channel 2 amplitude switch 40 are thereby utilized to control the amplitudes of the pulse trains outputted by their respective amplitude controls 34 and 36, with the outputs varying from no output to an pulse train amplitude equal to (or, optionally, greater than) the amplitude of the fixed amplitude pulse train from the pulse generator 32.

The channel 1 amplitude switch 38 and the channel 2 amplitude switch 40 also are each utilized to supply a signal to the start circuit 24. When the channel 1 amplitude switch 38 is adjusted to cause the channel 1 amplitude control 34 to provide no output, the channel 1 amplitude switch 38 will provide an enabling signal to the start circuit 24. Similarly, when the channel 2 amplitude switch 40 is adjusted to cause the channel 2 amplitude control 36 to provide no output, the channel 2 amplitude switch 40 will provide an enabling signal to the start circuit 24.

In order for the start circuit 24 to provide the start signal to the treatment timing circuit 26, enabling signals must be received from both the channel 1 amplitude switch 38 and the channel 2 amplitude switch 40. Thus, the start circuit 24 will not allow the stimulation device illustrated in FIG. 1 to begin operation unless both the channel 1 amplitude switch 38 and the channel 2 amplitude switch 40 are initially adjusted to cause the channel 1 amplitude control 34 and the channel 2 amplitude control 36, respectively, to be turned fully down so that no outputs will be initially supplied from them. This is an important safety feature of the stimulation device of the present invention.

In addition, if the start circuit 24 has previously produced a start signal without the on/off switch 22 subsequently having been turned off to power down the stimulation device, the start circuit 24 will not again operate to supply the start signal to the treatment timing circuit 26. This additional safety feature prevents the stimulation device from supplying therapy to a patient for an excessively long period.

If there are enabling signals supplied from the channel 1 amplitude switch 38 and the channel 2 amplitude switch 40, and if the start circuit 24 has not produced a start signal since being powered up, when a start switch 42 is actuated, 24 will operate to produce the start signal. When the treatment timing circuit 26 receives this start signal, the treatment timing circuit 26 will produce the timed drive signal for a preset period of time.

The preset period of time may be set by adjusting a cycle length switch 44. In the preferred embodiment, the preset period of time varies up to approximately 45 minutes, with between 20 and 45 minutes being the typical cycle length. Longer periods of treatment have been determined to be ineffective, and may cause the depletion of certain central nervous system neurochemicals and establish tolerance for the treatment.

For as long as the treatment timing circuit 26 produces the timed drive signal, the power switch 28 will supply the operation signal to the frequency generator 30. When the frequency generator 30 receives the operation signal, it will produce the pulsed signal, which is in turn supplied to the pulse generator 32. In the preferred embodiment, the pulsed signal is a train of spikes produced at a preset frequency.

The preset frequency may be set by adjusting a frequency switch 46. In the preferred embodiment, the preset frequency varies from 2 pulses per second to 10 pulses per second, with the lower frequencies being preferred. The frequency of the pulsed signal is the frequency at which the output pulse trains will be supplied from the stimulation device.

Thus, the pulse generator 32 will produce the fixed amplitude pulse train at the frequency set by the frequency generator 30. Each spike supplied from the frequency generator 30 will result in a single fixed amplitude pulse being supplied from the pulse generator 32. The morphology of the fixed amplitude pulses supplied by the pulse generator 32 will be discussed below in conjunction with FIG. 10.

The fixed amplitude pulse train supplied from the pulse generator 32 is varied in amplitude, independently, the channel 1 amplitude control 34, and by the channel 2 amplitude control 36. In the preferred embodiment, the pulse amplitudes of the output pulse trains supplied from the channel 1 amplitude control 34 and the channel 2 amplitude control 36 may be varied to produce an acceptable response. Different people require different stimulation levels to produce an acceptable response. The range of voltages produced by the device will be discussed below in conjunction with pulse morphology in FIG. 10.

Referring next to FIGS. 2 through 4, a clip top half 50 is illustrated. The clip top half 50 comprises a T-shaped segment 52, which is made from an insulative material such as plastic. The T-shaped segment 52 may be viewed as consisting of a vertical base portion and a horizontal top portion, as seen in the views of FIGS. 2 and 3. The T-shaped segment 52 is approximately an inch in width, and has two electrodes 54 and 56 mounted on the bottom side (the side illustrated in FIG. 3) thereof. The electrodes 54 and 56 are both made of an electrically conductive material, and form transcutaneous pads.

One of the electrodes 54 is located on the left side of the horizontal top portion of the T of the T-shaped segment 52 as seen in FIG. 3, and the other of the electrodes 56 is located on the right side of the horizontal top portion of the T of the T-shaped segment 52 as seen in FIG. 3. The electrodes 54 and 56 are spaced apart as seen in FIG. 3, and thus do not make electrical contact with each other.

The vertical base portion of the T of the T-shaped segment 52 has a pair of apertures 58 and 60 located therein. The aperture 58 is located near the bottom of the vertical base portion of the T of the T-shaped segment 52, as shown in FIGS. 2 and 3, while the aperture 60 is located nearer to the horizontal top portion of the T of the T-shaped segment 52. The apertures 58 and 60 will be used by a spring (not shown in FIGS. 2 through 4), which will hold the clip top half 50 and a clip bottom half (not shown in FIGS. 2 through 4) together in a pinching fashion.

Located on the bottom side of the T-shaped segment 52 on the sides of the vertical base portion of the T of the T-shaped segment 52 are two pivot arms 62 and 64, which extend outwardly and downwardly from the bottom surface of the T-shaped segment 52. The pivot arms 62 and 64 are located at the sides of the vertical base portion of the T of the T-shaped segment 52 adjacent the aperture 60. The pivot arm 62 is shown in a lateral view in FIG. 4.

Referring now to FIGS. 5 through 7, a clip bottom half 70 is illustrated. The clip bottom half 70 comprises a T-shaped segment 72, which is made from an insulative material such as plastic. The T-shaped segment 72 may be viewed as consisting of a vertical base portion and a horizontal top portion, as seen in the views of FIGS. 5 and 6. The T-shaped segment 72 is approximately an inch in width, and does not have any electrodes mounted thereon.

The vertical base portion of the T of the T-shaped segment 72 has a pair of apertures 78 and 80 located therein. The aperture 78 is located near the bottom of the vertical base portion of the T of the T-shaped segment 72, as shown in FIGS. 5 and 6, while the aperture 80 is located nearer to the horizontal top portion of the T of the T-shaped segment 72. The apertures 78 and 80 will be used by a spring (not shown in FIGS. 5 through 7), which will hold the clip top half 50 and the clip bottom half 70 together with the horizontal top portions of the T of the T-shaped segments 52 and 72 of the clip top half 50 and the clip bottom half 70, respectively, maintained in a pinching relationship.

Located on the top side of the T-shaped segment 72 slightly inwardly from the sides of the vertical base portion of the T of the T-shaped segment 72 are two tabs 82 and 84, which extend outwardly and upwardly from the top surface of the T-shaped segment 72. The tabs 82 and 84 are spaced slightly inwardly from the sides of the vertical base portion of the T of the T-shaped segment 72 adjacent the aperture 80. The tab 82 is shown in a lateral view in FIG. 7.

Referring next to FIG. 8, the clip top half 50 illustrated in FIGS. 2 through 4 and the clip bottom half 70 illustrated in FIGS. 5 through 7 are shown assembled together to form a clip 90. The clip top half 50 and the clip bottom half 70 are held together by a spring member 92, which fits through the apertures 58 and 60 in the T-shaped segment 52 of the clip top half 50 (FIGS. 2 and 3) and through the apertures 78 and 80 in the T-shaped segment 72 of the clip bottom half 70 (FIGS. 5 and 6).

The spring member 92 biases the horizontal top portions of the T-shaped segment 52 of the clip top half 50 and the T-shaped segment 72 of the clip bottom half 70 together in a pinching relationship, with the electrodes 54 and 56 on the horizontal top portion of the T-shaped segment 52 of the clip top half 50 being urged against the horizontal top portion of the T-shaped segment 72 of the clip bottom half 70.

The clip top half 50 and the clip bottom half 70 are maintained apart by the pivot arms 62 and 64 on the T-shaped segment 52. As shown in FIG. 8, the pivot arm 64 of the T-shaped segment 52 of the clip top half 50 fits adjacent to, outside of, and against the tab 84 of the T-shaped segment 72 of 70. Similarly, the pivot arm 62 of the T-shaped segment 52 of the clip top half 50 fits adjacent to, outside of, and against the tab 82 of the T-shaped segment 72 of the clip bottom half 70.

Referring next to FIG. 9, two ears 94A and 94B of a patient to be treated by the device of the present invention are illustrated, with a clip 90 placed on each of the ears 93A and 94B. The clip 90 placed on the right ear 94A is referred to as the clip 90A, while the clip 90 placed on the left ear 94B is referred to as the clip 90B. Similar parts on the clips 90A and 90B are referred to by the reference numerals given above with either the suffix -A or -B added.

The clips 90 are placed on the lobes of the ears 94A and 94B, which locations constitute the auricles of the ears 94A and 94B. In these positions, the electrodes 54A and 56A, and 54B and 56B, on each of the two clips 90A and 90B, respectively, make contact with the outer surface of the ears 94A and 94B, respectively, in areas from which superficial sprigs of the Vagus nerve are stimulated.

Thus, the electrodes 54A and 56A, and 56A and 56B, on the clips 90A and 90B, respectively, comprise transcutaneous pads which are used in pairs on the clips 90A and 90B, respectively, to stimulate the Vagus nerve. On each of the clips 90A and 90B, the electrodes 54A and 54B, respectively, are electrically connected to an electrical lead 96A and 96B, respectively, and the electrodes 56A and 56B, respectively, are electrically connected to an electrical lead 98A and 98B, respectively. The leads 96A and 98A, and 96B and 98B, will be used to supply electrical signals outputted from the channel 1 amplitude control 34 and the channel 2 amplitude control 36 (FIG. 1) to the clips 90A and 90B, respectively.

Referring now to FIG. 10, an exemplary bipolar pulse 100 is illustrated, with it being understood that while only a single pulse is illustrated, a train of pulses are utilized in the preferred embodiment. The bipolar pulse 100 used by the present invention is bipolar rather than unipolar to prevent polarization of the tissue being stimulated. As such, the pulse 100 consists of a positive voltage pulse 102 followed immediately by a negative voltage pulse 104.

Typically, the voltage pulses 102 and 104 will be generated by discharging capacitors by means of a pulsed transformer (not shown), as will be readily apparent to one skilled in the art. It will be appreciated that the area of the negative voltage pulse 104 is approximately the same as the area of the positive voltage pulse 102. This will result in each of the voltage pulses 102 and 104 sending approximately the same amount of charge into the tissue, which will prevent the tissue from becoming polarized.

It will be observed that the positive voltage pulse 102 is a truncated exponentially decaying waveform, while the negative voltage pulse 104 is a complete exponentially decaying waveform. In addition, it should be noted that the negative voltage pulse 104 decays at a much faster rate than does the positive voltage pulse 102. Finally, note that the initial magnitude of the negative voltage pulse 104 is greater than the initial magnitude of the positive voltage pulse 102.

Referring again to FIG. 1 in addition to FIG. 10. in the preferred embodiment, the pulse generator 32 generates the full voltage of the bipolar pulse 100 illustrated in FIG. 10. The amplitude controls 34 and 36 are used to moderate the amplitude of the bipolar pulse 100 generated by the pulse generator 32 by a factor of between zero and one. Thus, the pulse generator 32 generates a relatively large voltage bipolar pulse 100, and the amplitude controls 34 and 36 are used to reduce the amplitude of the bipolar pulse 100 to the desired level.

In the preferred embodiment, the full amplitude of the positive voltage pulse 102 of the bipolar pulse 100 is characterized by a peak amplitude of approximately +80 Volts, and the full amplitude of the negative voltage pulse 104 of the bipolar pulse 100 is characterized by a peak amplitude of approximately −120 Volts. The magnitude of the negative voltage pulse 104 is thus approximately one and one-half times the magnitude of the positive voltage pulse 102 in the preferred embodiment. The width of the positive voltage pulse 102 of the bipolar pulse 100 in the preferred embodiment is approximately 0.2 milliseconds.

The operation of the device of the present invention may now be explained with reference to FIGS. 1, 9, and 10. The clips 90A and 90B are applied to the ears 94A and 94B, respectively. The leads 96A and 98A from the clip 90A are attached to the output terminals of the channel 1 amplitude control 34. The leads 96B and 98B from the clip 90B are attached to the output terminals of the channel 2 amplitude control 36.

The levels of the amplitude switches 38 and 40 are turned fully down, which will adjust the output amplitude from the amplitude controls 34 and 36 to zero when the pulse generator 32 is operating. If the amplitude controls 34 and 36 are not set to zero, the start circuit 24 will prevent the device from producing any output pulses. The frequency switch 46 is adjusted to set the desired repetition rate or frequency at which the bipolar pulses 100 will be produced. In the preferred embodiment, the repetition rate or frequency of the bipolar pulse 100 is variable between 2 pulses per second and 10 pulses per second, with lower repetition rates or frequencies being preferable.

The cycle length switch 44 is adjusted to set the length of the treatment time, which is the length of the period during which the pulse generator 32 will produce pulses before being turned off by the treatment timing circuit 26. In the preferred embodiment, the cycle length is variable up to 45 minutes, with the preferred period of treatment being approximately 25 minutes. Note that it has been determined that addictions which are difficult to treat will require greater periods of treatment, up to the 45 minute limit.

At this point, the on/off switch 22 is turned on and the start switch 42 is actuated to initiate the treatment. The amplitude switches 38 and 40 are adjusted to increase the amplitude of the variable amplitude pulse train supplied by the amplitude switches 38 and 40 to the clips 90A and 90B. The amplitude used to treat each patient may vary, with the amplitude being increased until the patient responds.

Typically, to treat withdrawal symptoms, the treatment will be used on a patient once or twice per day for a period of between two and six days, which is the length of the withdrawal phase. For pain treatment, for reduction of stress, or for general muscle relaxation, the treatments may be provided on an as-needed basis. Note that it is possible to treat only one ear 94 instead of both ears 94A and 94B, but that optimal results are ensured by treating both ears 94A and 94B.

It may therefore be appreciated from the above detailed description of the preferred embodiment of the present invention that it teaches both a device and a related method of operating the device which are capable of efficiently and effectively treating emotionally or environmentally induced stress, promoting endogenous pain control, and assisting in muscle relaxation. Further, the apparatus and the optimized technique of applying therapy of the present invention are highly useful in the treatment of substance abuse, enabling the withdrawal from use of the substance with substantially minimized withdrawal symptoms. The device and method of the present invention also require only a relatively short treatment session, with only a relatively small number of treatment sessions being required for successful treatment.

The device and the method of the present invention are both safe and efficacious in every way. In addition, the apparatus and method of the present invention use a principle of operation which prevents the undesirable polarization of body tissue during operation. It is a further advantage of the device and method of the present invention that they do not deplete neurochemicals during their operation, and that their operation will not result in a tolerance for the treatment being established.

The apparatus of the present invention is of a construction which is both durable and long lasting, and it also requires little or no maintenance to be provided by the operator. It features both inexpensive construction and inexpensive operation, thereby enhancing its market appeal to afford it the broadest possible market. Finally, all of the aforesaid advantages and objectives of the present invention are achieved without incurring any substantial relative disadvantage.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A device for providing transcutaneous nerve stimulation, comprising:

pulse generator means for providing an output waveform comprising a series of electrical pulses;

amplitude adjustment means for adjusting the amplitude of said output waveform supplied by said pulse generator means between zero amplitude and full amplitude;

repetition rate adjustment means for adjusting the rate at which said electrical pulses are repeated in said output waveform;

cycle length adjustment means for adjusting the length of time that said output waveform will be provided by said pulse generator means;

start switch means for initiating the provision of said output waveform from said pulse generator means;

reset switch connected to said pulse generator means for resetting said device for providing transcutaneous nerve stimulation;

first safety interlock means for preventing said start switch means from repetitively initiating the provision of said output waveform from said pulse generator means without said device first being reset with said reset switch means; and a first pair of transcutaneous pad electrodes for placement on a surface of the body of a patient to be treated, said first pair of transcutaneous pad electrodes being electrically connected to said pulse generator means whereby said output waveform is supplied by said pulse generator means to said first pair of transcutaneous pad electrodes.

2. A device as disclosed in claim 1, wherein said pulse generator means comprises:

means for generating a series of biphasic pulses comprising a positive voltage pulse and a negative voltage pulse.

3. A device as disclosed in claim 2, wherein said pulse generator means is operable to cause said negative voltage pulse to immediately follow said positive voltage pulse in each of said biphasic pulses.

4. A device as disclosed in claim 2, wherein said pulse generator means is operable to cause the area of said negative voltage pulse to be approximately equal to the area of said positive voltage pulse, the polarization of tissue stimulated by said biphasic pulses thus being prevented.

5. A device as disclosed in claim 2, wherein said pulse generator means is operable to cause said positive voltage pulse to be a truncated exponentially decaying waveform, and wherein said pulse generator means is operable to cause said negative voltage pulse to be a complete exponential decaying waveform.

6. A device as disclosed in claim 5, wherein said pulse generator means is operable to cause the width of said positive voltage pulse to be fixed at approximately 0.2 milliseconds.

7. A device as disclosed in claim 5, wherein said pulse generator means is operable to cause the initial magnitude of said negative voltage pulse to be approximately one and one-half times the initial magnitude of said positive voltage pulse.

8. A device as disclosed in claim 7, wherein the initial magnitude of said positive voltage pulse is approximately 80 volts when said amplitude adjustment means is set to adjust said output waveform to full amplitude, and wherein the initial magnitude of said negative voltage pulse is approximately 120 volts when said amplitude adjustment means is set to adjust said output waveform to full amplitude.

9. A device as disclosed in claim 1, wherein said repetition rate adjustment means is operable to adjust the repetition rate of said electrical pulses between 2 pulses per second and 10 pulses per second.

10. A device as disclosed in claim 1, wherein said cycle length adjustment means is operable to adjust the length of time that said output waveform will be provided by said pulse generator means up to approximately 45 minutes.

11. A device as disclosed in claim 1, wherein said reset switch means comprises:

an on/off switch for selectively, alternately supplying or not supplying power to operate said device for providing transcutaneous nerve stimulation, said on/off switch resetting said device when it is turned off and then on again.

12. A device as disclosed in claim 1, additionally comprising:

second safety interlock means for preventing said start switch means from repetitively initiating the provision of said output waveform from said pulse generator means without said amplitude adjustment means first being set to adjust the amplitude of said output waveform to zero amplitude.

13. A device as disclosed in claim 1, additionally comprising:

means for retaining said first pair of transcutaneous pad electrodes in contact with the surface of the body of a patient.

14. A device as disclosed in claim 13, wherein said means for retaining said first pair of transcutaneous pad electrodes in contact with the surface of the body of a patient comprises:

a clip having two clip halves located adjacent each other in a pivoting relative relationship, said clip having jaws at one end of each of said clip halves which jaws may be opened and closed by pivoting said clip halves relative to each other, said clip being biased by a spring into a closed position in which said jaws are closed, said transcutaneous pad electrodes being mounted in spaced-apart position on one of said clip halves at said one end of said one of said clip halves on the side of said one of said clip halves facing the other of said clip halves.

15. A device as disclosed in claim 14, wherein said clip is arranged and configured to allow said clip to be placed on the lobe of an ear of a patient, said transcutaneous pad electrodes being arranged and configured on said clip to stimulate superficial sprigs of the Vagus nerve located in the auricle of the ear.

16. A device as disclosed in claim 1, additionally comprising:

a second pair of transcutaneous pad electrodes for placement on a surface of the body of a patient to be treated, said second pair of transcutaneous pad electrodes being electrically connected to said pulse generator means whereby said output waveform is supplied by said pulse generator means to said second pair of transcutaneous pad electrodes.

17. A device as disclosed in claim 16, wherein said amplitude adjustment means is operable to independently adjust the amplitude of said output waveform provided to each of said first and second pairs of transcutaneous pad electrodes.

18. A device for providing transcutaneous nerve stimulation, comprising:

pulse generator means for providing an output waveform comprising a series of electrical pulses;

amplitude adjustment means for adjusting the amplitude of said output waveform supplied by said pulse generator means between zero amplitude and full amplitude;

repetition rate adjustment means for adjusting the rate at which said electrical pulses are repeated in said output waveform;

cycle length adjustment means for adjusting the length of time that said output waveform will be provided by said pulse generator means;

start switch means for initiating the provision of said output waveform from said pulse generator means;

reset switch connected to said pulse generator means for resetting said device for providing transcutaneous nerve stimulation;

first safety interlock means for preventing said start switch means from repetitively initiating the provision of said output waveform from said pulse generator means without said device first being reset with said reset switch means;

second safety interlock means for preventing said start switch means from repetitively initiating the provision of said output waveform from said pulse generator means without said amplitude adjustment means first being set to adjust the amplitude of said output waveform to zero amplitude;

a first pair of transcutaneous pad electrodes for placement on a surface of the body of a patient to be treated, said first pair of transcutaneous pad electrodes being electrically connected to said pulse generator means whereby said output waveform is supplied by said pulse generator means to said first pair of transcutaneous pad electrodes;

clip means for retaining said first pair of transcutaneous pad electrodes in contact with the surface of one ear of a patient;

a second pair of transcutaneous pad electrodes for placement on a surface of the body of a patient to be treated, said second pair of transcutaneous pad electrodes being electrically connected to said pulse generator means whereby said output waveform is supplied by said pulse generator means to said second pair of transcutaneous pad electrodes and clip means for retaining said second pair of transcutaneous pad electrodes in contact with the surface of the other ear of a patient.

19. A device for providing transcutaneous nerve stimulation, comprising:

means for providing a pulsatile electrical output waveform;

means for adjusting the amplitude of said pulsatile electrical output waveform;

means for adjusting the rate at which pulses are repeated in said pulsatile electrical output waveform;

means for adjusting the length of time that said pulsatile electrical output waveform will be provided;

means for initiating the provision of said pulsatile electrical output waveform;

means for resetting said device for providing transcutaneous nerve stimulation connected to said means for providing a pulsatile electrical output wave form;

means for preventing the repetitive initiation of the provision of said pulsatile electrical output waveform without said device first being reset; and a first pair of transcutaneous pad electrodes for placement on a surface of the body of a patient to be treated, said first pair of transcutaneous pad electrodes being supplied with said pulsatile electrical output waveform.

20. A method of providing transcutaneous nerve stimulation, comprising:

providing an output waveform comprising a series of electrical pulses from a pulse generator;

adjusting the amplitude of said output waveform supplied by said pulse generator between zero amplitude and full amplitude;

adjusting the rate at which said electrical pulses are repeated in said output waveform;

adjusting the length of time that said output waveform will be provided by said pulse generator;

initiating the provision of said output waveform from said pulse generator;

preventing the repetitive initiation of the provision of said output waveform from said pulse generator without said device first being reset; and supplying said output waveform to a first pair of transcutaneous pad electrodes for placement on a surface of the body of a patient to be treated, said first pair of transcutaneous pad electrodes being electrically connected to said pulse generator.

* * * * *